United States Patent [19]

Saros et al.

[11] Patent Number: 4,853,336

[45] Date of Patent: Aug. 1, 1989

[54] SINGLE CHANNEL CONTINUOUS FLOW SYSTEM

[75] Inventors: Stephen Saros, Wantagh; John L. Smith, New City; Michael M. Cassaday, Peekskill, all of N.Y.; Rand E. Herron, Wilton, Conn.; Milton H. Pelavin, Chappaqua, N.Y.

[73] Assignee: Technicon Instruments Corporation, Tarrytown, N.Y.

[21] Appl. No.: 10,236

[22] Filed: Feb. 2, 1987

Related U.S. Application Data

[63] Continuation of Ser. No. 798,509, Nov. 15, 1985, abandoned, which is a continuation of Ser. No. 441,881, Nov. 15, 1982, abandoned.

[51] Int. Cl.$^4$ .............................................. G01N 35/08
[52] U.S. Cl. ........................................ 436/53; 422/81; 422/82; 436/52
[58] Field of Search ...................... 422/82, 81; 436/53, 436/52; 73/864.12, 864.21, 864.22, 861.05; 138/26; 366/106, 262, 139, 341; 324/453, 439; 55/15, 158

[56] References Cited

U.S. PATENT DOCUMENTS

| | | | |
|---|---|---|---|
| 2,910,830 | 11/1959 | White .................................. | 138/26 X |
| 2,967,764 | 1/1961 | Skeggs ................................ | 422/82 X |
| 3,047,367 | 7/1962 | Kessler ............................... | 422/82 X |
| 3,241,921 | 3/1966 | Ferrari ................................ | 422/82 |
| 3,479,141 | 11/1969 | Smythe et al. ..................... | 436/53 |
| 3,479,142 | 11/1969 | Israeli et al. ...................... | 436/53 X |
| 3,624,223 | 11/1971 | Smythe ............................... | 422/82 X |
| 3,826,615 | 7/1974 | Smythe et al. ..................... | 436/53 |
| 3,855,098 | 12/1974 | Fletcher ............................. | 204/409 X |
| 4,121,466 | 10/1978 | Reichler et al. ................... | 73/864.22 |
| 4,253,846 | 3/1981 | Smythe et al. ..................... | 422/82 X |
| 4,302,223 | 11/1981 | Booth .................................. | 55/158 |
| 4,328,185 | 5/1982 | Reasons et al. ................... | 422/81 X |
| 4,398,925 | 8/1983 | Trinh et al. ........................ | 55/15 |

Primary Examiner—Michael S. Marcus
Attorney, Agent, or Firm—Jeffrey M. Greenman

[57] ABSTRACT

A continuous flow system is disclosed in which successive liquid segments are established containing different related components of a fluid package, such as an analysis mixture, separated by at least one immiscible segment, passed along a first section of a conduit, combined in a second section of the conduit and mixed while passing along a third section of the conduit, so as to provide a completely mixed segment. This system permits the delayed on-line mixing of different components of an analysis mixture, such as samples with reagents or diluents, as well as mixing and interaction of such components in a single conduit.

11 Claims, 5 Drawing Sheets

SINGLE CHANNEL CONTINUOUS FLOW SYSTEM

This is a continuation of application Ser. No. 798,509, filed Nov. 15, 1985, now abandoned, which is a continuation of Ser. No. 441,881, filed Nov. 15, 1982, now abandoned.

BACKGROUND OF THE INVENTION

1. Field of the Invention

The present invention relates to a fluid handling system, apparatus and method. It is particularly useful for mixing liquid samples with previously separated processing liquids, such as reagents or diluents, in continuous flow analyzers.

2. Brief Description of the Prior Art

Automated apparatus for the analysis of liquid samples as a flowing stream was disclosed by Skeggs in U.S. Pat. Nos. 2,797,149 and 2,879,141, both assigned to the instant assignee. In this basic apparatus, the liquid samples are sequentially aspirated from storage containers into a conduit, each sample being separated from the next sample by succesive segments of air. Air is introduced between successive segments of an individual sample to promote intrasample mixing and between samples to prevent intersample contamination. Such air/sample sequences can be alternated with air/wash liquid sequences to further insure against carryover. As illustrated by Ferrari in U.S. Pat. No. 2,933,293, also assigned to the instant assignee, a junction in the conduit continually introduces a processing liquid, such as a reagent, into the alternating sequence of air and sample segments and, also, into wash segments when present. In apparatus such as that described above, the fluid stream containing air segments and segments of combined sample and processing fluid can be "debubbled" immediately before entering a flow cell through which the reacted samples are read. Thus, the successive sample segments contact one another just before entry into the flow cell. The debubbler was positioned adjacent to the flow cell to prevent undesirable intermixing between liquid segments. Alternatively, as in high throughput systems, the air segments can be passed through the flow cell.

Ferrari et al, U.S. Pat. No. 3,109,713, assigned to the instant assignee, also discloses an analysis apparatus in which procesing fluids, such as reagents, are continuously introduced into a stream of alternating air and sample segments as shown in the juncture of conduits 42 and 44 in FIG. 1. A series of substantially identical segments of a single processed sample are passed through a debubbler. The air is abstracted to consolidate and blend the segments of processed liquid which are passed through a flow cell. Debubbling and blending was done to prevent disruption of colorimeter operation by the optical properties of the air bubbles.

Smythe et al, U.S. Pat. No. 3,479,141, likewise assigned to the instant assignee, discloses a transport system for automatic analysis apparatus in which a series of aqueous liquid samples are processed as a flowing fluid stream with substantially no contamination between segments. A fluoropolymer conduit and intersample carrier segments of silicone are used. The silicone, in effect, encapsulates the aqueous liquid segments during passage along the conduit. Thus, contamination between successive liquid segments is substantially completly eliminated. Further, in such improved apparatus, it has been recognized that debubbling defeats the principal advantages of this approact.

Smythe et al, U.S. Pat. No. 3,804,593, also assigned to the instant assignee, discloses an analysis apparatus having a first tube which receives samples from vessels on a turntable and a second tube which receives reagent liquid from a stationary reagent container. Both tubes are concurrently inserted into their respective containers repeatedly to provide a flowing stream of segments of liquid sample interspersed by air segments and a similarly segmented stream of reagent. These streams are merged to form an alternating sequence of air and sample/reagent segments which are then analyzed. As in the other patents discussed, each of the samples is reacted on-line with only a single reagent, the reaction beginning immediately upon the reagent being introduced into the system. No capability for testing samples with only selected reagents is provided. Since many samples are run for only one or a few particular analyses, this is wasteful of time and reagents and thus, more costly to the patient.

In each of the prior art systems, the reagent is reactive with the sample immediately upon introduction into the system. Accordingly, such systems are not suitable for performing two-stage reactions, i.e., those in which a first reaction must be completed before a second reaction is commenced. Such reactions would require that the reagents be introduced at different points or locations along the system. This would require complication of the conduit system and, also, present severe phasing problems, particularly when the system is adapted to perform different analyses, on a random basis, along a same conduit. Such phasing problems would be especially severe in high flow rate systems using small volumes of sample. For these reasons, prior art systems have generally been adapted only to perform single-stage reactions.

SUMMARY OF THE INVENTION

An entirely new concept in controlled fluid handling has been developed, which is particularly adapted for use in continuous flow analytical systems. This concept provides selective reagent access capability over a wide range of assay potential, combined with a throughput and time-delayed fluid segment mixing capacity never before available. Only the specific assays requested for a particular sample are run, and they can be processed in any order. These combined advantages are achieved in a system of elegant simplicity and require no phased introduction of reagents at spaced points along the conduit or channel. All of the samples to be assayed and all of the reagents required are introduced through a single aspirating probe. All tests for every sample, whether requiring a one-stage or two-stange reaction, are processed through a single analytical channel.

The present invention provides for the controlled or delayed intermixing of certain successive liquid segments, on-line, in continuous flow systems, to achieve the numerous advantages referred to above. Therefore, the invention makes possible the delayed intermixing of separated liquid segments, such as by displacement, fragmentation or physical removal of intervening immiscible segments, at selected points along a conduit while flow of the liquid stream continues. Of the separated segments, one segment can be a sample while the segment with which it is combined can be a reagent, diluent or other liquid. Mixing of the combined segments is completed during flow along the remainder of the conduit, so as to deliver a completely mixed segment to succeeding elements of the system.

Accordingly, the present invention provides a continuous flow system which comprises (a) a conduit having first, second and third sections; (b) means for passing a fluid stream therethrough; (c) means for introducing a fluid stream comprising successive liquid segments separated by at least one immiscible segment into said first conduit section, said separated segments being different related components of a fluid package; (d) means for combining said separated liquid segments along said second conduit section to permit complete mixing of the segments while passing along said third conduit section to provide a completely mixed segment; and (e) means for receiving the completely mixed segment from said third conduit section. In the preferred embodiment of the invention, the walls of that portion of the conduit where coalescence occurs, are completely closed and have an expanded diameter sufficient to render an immiscible intervening segment, such as an air bubble, non-occluding, whereby the segments are forced to coalesce.

The invention further provides a continuous flow method of passing a fluid stream through first, second and third sections of a conduit, wherein the improvement comprises the steps of (a) introducing successive liquid segments separated by an immiscible segment into said first conduit section, said separated segments being different related components of a fluid package; (b) combining said separated liquid segments along said second conduit section to permit complete mixing of the segments while passing along said third conduit section; and (c) receiving said completely mixed segments from said third conduit section. In the preferred embodiment as described, the combined reagent and sample segment so created is followed by an additional immiscible segment, which coalesces with the previously intervening, and now non-occluding, immiscible segment.

BRIEF DESCRIPTION OF THE DRAWINGS

FIGS. 5A–5C are sequential diagrammatic views illustrating the combination of separated liquid segments and immiscible segments along the conduit as contemplated by an alternative embodiment of the invention.

DESCRIPTION OF THE PREFERRED EMBODIMENTS

Although specific terms are used in the following description for clarity, they refer only to the particular embodiment(s) selected for illustration, and are not intended to limit the scope of the invention.

The system of the present invention is particularly suitable for continuous flow analyzers which are used to detect an analyte in a liquid sample. Sample fluids on which tests are performed include biological, physiological, industrial, environmental and other types of liquids. Of particular interest are biological fluids such as whole blood, serum, plasma, urine, cerebrospinal fluid, broth and other culture media and supernatants as well as fractions of any of them. Physiological fluids of interest include infusion solutions, buffers, preservatives or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated as within the meaning of this term as used and can, likewise, be assayed in accordance with the invention.

Figure 1:
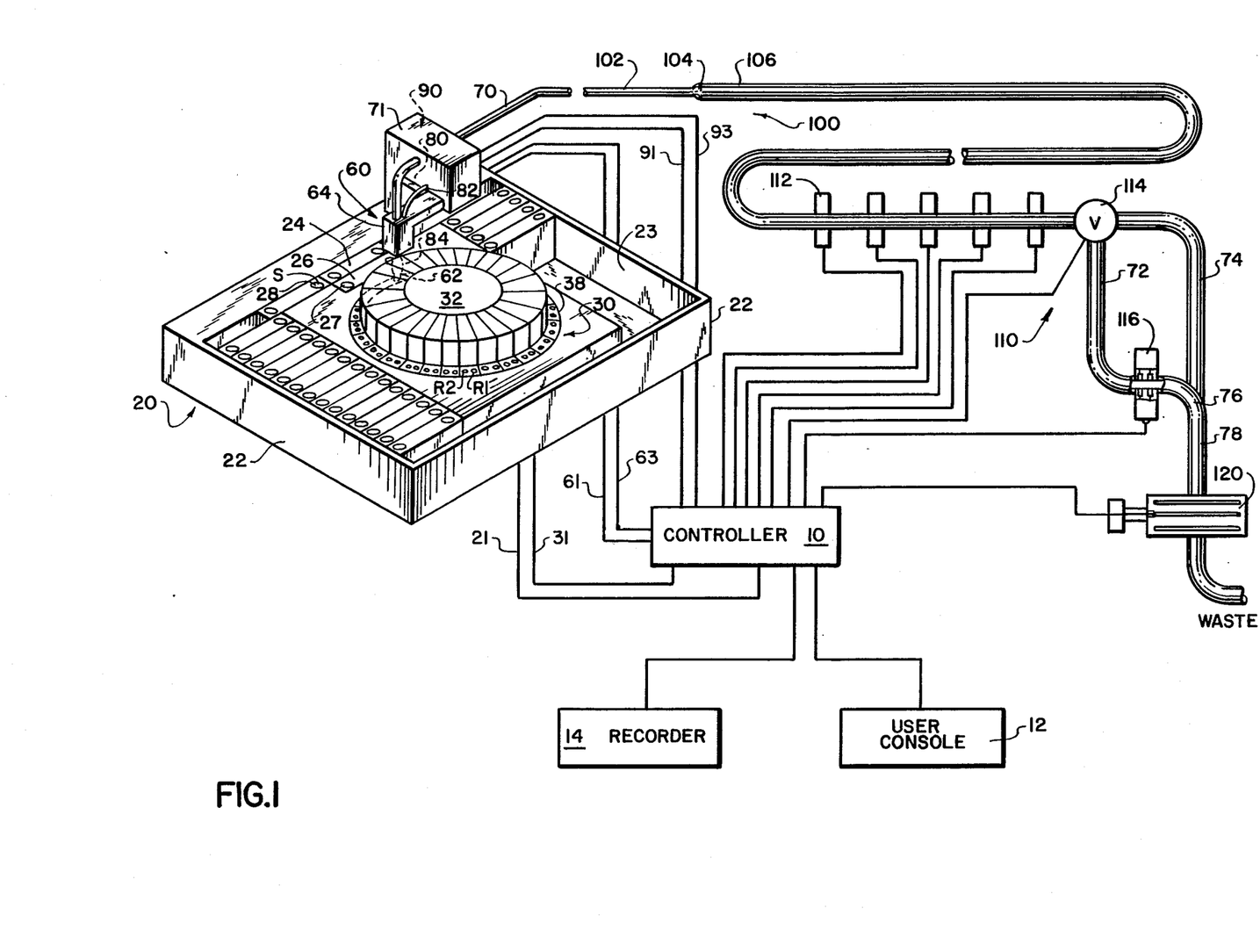
FIG. 1 illustrates a preferred embodiment of the single channel continuous flow system of the present invention.

Referring now to FIG. 1, controller 10 is a general purpose digital computer with a stored (fixed) program which is connected with user console 12 and recorder 14. User console 12 conventionally includes a cathode ray tube (CRT) terminal and keyboard. Recorder 14 conventionally includes a printer for recording the test data for each analysis. Controller 10 instructs, monitors and controls the sequence and coordination of system operations, as more fully described below, as well as calculates and monitors the quality of results and provides data output in a variety of formats.

Sample assembly 20 includes sample table 22 which holds a plurality of sample carrier blocks 24 and a shuttle carrier 26. Each such carrier block 24 carries a plurality of sample vessels 28 containing a body fluid sample S (e.g. serum). As directed by controller 10 along lead 21, sample blocks 24 are sequentially advanced, in an clockwise direction, so as to be successively positioned to present sample vessels 28 carried thereon, in turn, for aspiration. Adjacent carrier block 24, presented for aspiration, is shuttle carrier 26 which holds ancillary fluid vessels 27 containing ancillary fluids such as calibrators, dyes, controls, and the like. When the system has completed the necessary aspiration of sample S from all of the sample vessels 28 of a particular carrier block 24, that sample carrier block 24 is moved to a holding area 23 of sample table 22.

Reagent assembly 30 includes reagent turntable 32 connected to bidirectional rotational drive means (not shown). The drive means is activated by controller 10 along lead 31 connected to the non-illustrated drive means to impart a metered rotation of reagent turntable 32 to present a selected reagent dispenser 38 for aspiration. Reagent turntable 32 is provided with one row of reagent dispensers 38. Each of reagent dispensers 38 contains the components necessary to dispense the first reagent $R_1$ and the second reagent $R_2$ of two reagents necessary for two-stage reaction with a sample S. The drive means rotates turntable 32 slightly after aspiration of first reagent $R_1$ to present the second reagent $R_2$ for aspiration. Reagent dispenser 38 is described in more detail with reference to later drawings.

Probe assembly 60 includes probe 62 which aspirates sample, reagent and air into conduit 70. Probe 62 is carried at one end of probe arm 64, the other end of which is connected to bidirectional linear drive means (not shown). Directed by controller 10 along lead 61, the drive means imparts bidirectional horizontal movement of probe arm 64 to position probe 62 over a selected sample vessel 28, ancillary fluid vessel 27, or reagent dispenser 38 which has been presented for aspiration. Additionally, the drive means imparts bidirectional vertical movement, under control of controller 10 along lead 63, to probe 62 which is thereby lowered into sample vessel 28 or reagent dispenser 38 and, after aspiration, raised. Aspiration of fluids is effected by pumping means which is located at the downstream end of the system and is more fully described below. The aspirated liquid segments are passed along the conduit. Preferably, the inner surface of the conduit is coated with an immiscible liquid, such as described in Smythe et al, U.S. Pat. No. 3,479,141 to prevent undesirable carryover contamination.

Housing 71 encloses an immiscible liquid dispenser assembly 80 which includes a reservoir (not shown) which introduces immiscible liquid IL into the inlet of feed tube 82, the outlet of which connects to applicator shroud 84. Immiscible liquid IL is dispensed from applicator shroud 84 onto the outer surface of probe 62. Immiscible liquid IL preferentially wets and forms a continuous film over the outer and inner surfaces of probe 62, the inner surface of conduit 70 and other conduits of the system to prevent the carryover contamination referred to above. In operation, probe 62 passes through a lens of immiscible liquid IL formed, manually or by an automated mechanism, on the surface of reagent liquids of reagent dispenser 38, as described with reference to later drawings, to aspirate an aliquot of reagent and immiscible liquid IL. The immiscible liquid IL which is thereby introduced into probe 62 replaces the immiscible liquid IL used throughout the analyzer and is, itself, replaced by immiscible liquid IL flowing down the outside of probe 62. For example, if probe 62, conduit 70 and other conduits of the system are formed of polytetrafluoroethylene, fluorocarbon can be used as immiscible liquid IL. This is described in greater detail in a co-filed application entitled "INTEGRAL REAGENT DISPENSER", now U.S. Pat. No. 4,515,753 and assigned to the instant assignee.

Housing 71 also encloses metering apparatus 90 which uses segment position sensing in conjunction with flow-stopping valve(s) to control (meter) sample/reagent aspiration into conduit 70 so as to define a fluid package to perform a particular analysis. Multiple detectors (sensors) and valves can generate different segment patterns of air/liquid volumes. In a preferred embodiment, metering apparatus 90 aspirates, in order, (1) an aliquot of a sample to be analyzed, and (2) and aliquot of a first reagent, which combines with the sample aliquot in conduit 70 to form a first liquid segment, i.e., the first stage of a two-stage reaction, (3) a small segment of air, (4) an aliquot of a second reagent which constitutes a second liquid segment, i.e., the second stage of a two-stage reaction, and (5) a large segment of air. Controller 10 coordinates the operation of assembly 20, reagent assembly 30, prove assembly 60 and immiscible liquid IL dispenser assembly 80 with each other and with metering assembly 90, an example fo which is described in more detail with reference to later drawings. Each fluid package contains the components necessary for one of the may individual analyses which can be performed on a particular sample. Multiple aliquots of a particular sample can be aspirated, each in association with a separate test package containing reagents appropriate for the analysis of interest. Successive test packages are thereby established containing reagents for analyses which can be selected in any order.

Segment combining zone 100 of the invention includes a narrow section 102 through which segments, established as described above, flow sequentially into expanding diameter flotation zone 104 and, thereafter, to an enlarged mixing zone 106. The final diameter of flotation zone 104 is equal to that of mixing zone 106. The first liquid segment comprising a mixture of the first reagent and the sample, enters flotation zone 104. The succeeding small air segment, which is of insufficient volume of occlude flotation zone 104 enters, becomes buoyant in and floats to the top of flotation zone 104. Thereafter, the second liquid segment, comprising the second reagent or a diluent for the first segments enters flotation zone 104 and begins to mix with the first liquid segment, forming a new segment which is the combination of the two, previously separated, liquid segments. Following combination of the liquid segments, mixing of and the reaction between sample, first reagent and second reagent segments begin. The succeeding large air segment enters flotation zone 104 and is of sufficient volume to occlude such zone. The large air segment coalesces with the small non-occluding air segment therein. The "combined" air segment and combined liguid segments enter enlarged section 106. The combined liquid segments are continually mixed during travel through subsequent portions of the system and are thereafter analyzed. The "combined" air segment serves to maintain successive combined liquid segments, each resulting from a test package, discrete during flow along the system. This sequence of events and alternate embodiments are described in further detail with reference to later drawings.

The successive combined liquid segments, separated from each other by an occluding air segment, flow through conduit 70 and into detector assembly 110, which includes a series of colorimeters 112, a bypass valve 114 and an ion-specific electrode 116. Colorimeters 112 are selectively activated by controller 10 based on the type of analysis to be performed. Static or kinetic assays, using one or more of colorimeters 112, can be performed over a broad spectrum of wavelengths. Bypass valve 114 directs flow of a test package to branch conduit 74. Branch conduits 72 and 74 come together at juncture 76, which is connected to pump tube 78 of peristaltic pump 120. Peristaltic pump 120 operates to provide the motive force for pulling all fluids into and through the system. Fluids which pump 120 has pulled through the system are passed to waste.

Figures 2, 3, 3A:
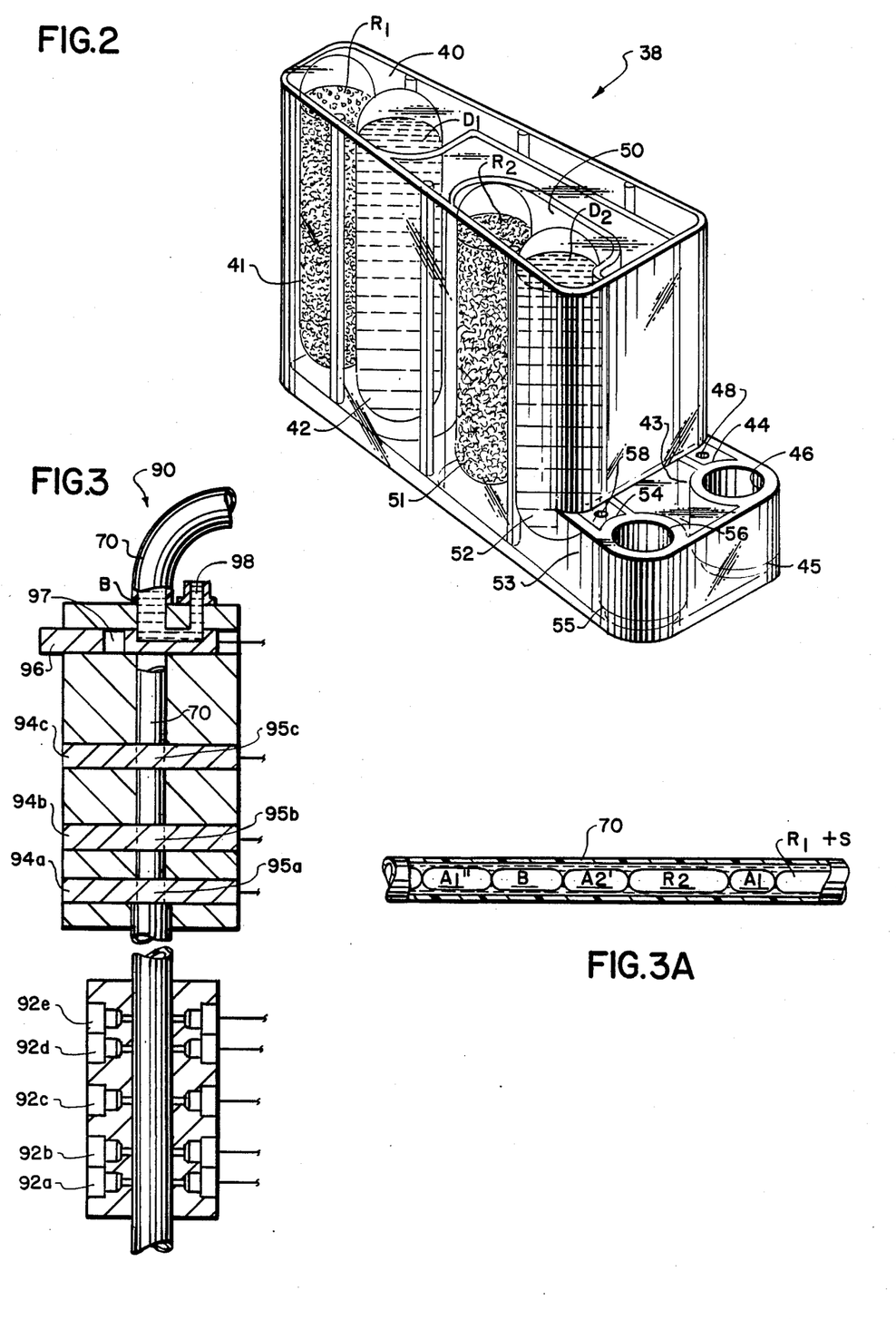
FIG. 2 is an enlarged view of the reagent dispenser illustrated in FIG. 1.
FIG. 3 is a detailed view of the metering assembly referred to in FIG. 1.
FIG. 3A illustrates the sequence of separated segments provided in accordance with a preferred method using the metering apparatus of FIG. 3.

FIG. 2 illustrates two-reagent dispenser package 38 in greater detail. The reagent dispenser illustrated is of an inert material, such as plastic, and contains corresponding reagents $R_1$ and $R_2$ of a particular assay composition. The components of dispenser 38 which relate to reagents $R_1$ and $R_2$ are substantially identical, but for their position. Reagent dispenser 38 includes two reagent supply compartments 40 and 50, each of which encloses two breakable capsules. Capsules 41 and 51 contain lyophilized reagents $R_1$ and $R_2$, respectively. Capsules 42 and 52 contain reconstituting diluents $D_1$ and $D_2$, both of which are usually buffers. Reagent dispenser 38 has flexible side walls which permit external pressure to break reagent capsules 41 and 51 and reconstituting diluent capsules 42 and 52. This is done while reagent dispenser 38 is tilted on its back. It is then gently rocked to reconstitute and mix reagents $R_1$ and $R_2$ concurrently. When reagent dispenser 38 is righted and positioned on a turntable, as shown in the drawing discussed above, reagents $R_1$ and $R_2$ flow through supply ports 43 and 53 into reagent troughs 44 and 54, respectively. At the outlet of reagent troughs 44 and 54 are filters 45 and 55. Reagents $R_1$ and $R_2$, respectively, pass through filters 45 and 55 into dispensing wells 46 and 56. A fluid level equilibrium is established between reagent supply compartments 40 and 50 and their respective dispensing wells 46 and 56. Both dispensing wells have a hydrophilic interior surface. The dimensions and hydrophilic surfaces of dispensing wells 46 and 56 combine with the wetting characteristics of reagents $R_1$ and $R_2$, respectively, to form a concave reagent meniscus in each well which is reliably suitable to position a drop of immiscible liquid thereon. A drop of immiscible liquid IL is positioned on each meniscus, either manually or from an immiscible liquid dispenser as described above. Immiscible liquid IL is immiscible with all other fluids in the system, including sample, reagent buffer and air and forms discrete lenses (so-called because of their shape) on the meniscus of reagents $R_1$ and $R_2$, respectively, due to the balance of interfacial tensions of the three fluids (reagent, immiscible liquid and air) at the points of three-phase contact which constitute the periphery of the lens. These lenses 47 and 57 are centrally located by the concave shape of each meniscus.

The analysis system probe (not shown), preferably made of a solid fluoropolymer, sequentially intersects an immiscible fluid lens and reconstituted reagent liquid, both of which are aspirated into the analysis system. During system operation, a certain amount of reagent is aspirated from dispensing wells 46 and 56. As this occurs, the level of reagent in reagent trough 44 and 54 is also lowered. When the level falls enough to partially expose either of supply ports 43 and 53 to air, air flows into respective reagent supply compartments 40 and 50 to replace that volume of reagent which is permitted to flow out into reagent troughs 44 or 54. Vents 48 and 58 allow introduction of air to troughs 44 and 54. Thus, the reagent levels in dispensing wells 46 and 56 remain within a range until the reagent supply is nearly depleted. Upon depletion of either of reagent $R_1$ or $R_2$, dispenser 38 is discarded. Reagent dispenser 38 is a preferred embodiment of the reagent package which is the subject of a co-filed application entitled "INTEGRAL REAGENT DISPENSER", now U.S. Pat. No. 4,515,753.

FIG. 3 illustrate metering assembly 90 including (a) an array of position sensors 92a-92e, such as photodetectors, specific ones of which are programmed to detect the interface between a selected air segment and following liquid segment, and (b) stop valves 94a-94c and buffer valve 96 which are positioned a specific distance downstream of the array of position sensors. Stop valves 94a-94c, respectively form valve ports 95a-95c. Buffer valve 96 includes valve port 97 and buffer injection port 98 which introduces buffer B from a reservoir (not shown) into conduit 70 so as to bisect the large air segment of each test package.

The volume of each aspirated segment is established by the position of the appropriate one of detectors 92a-92e relative to the point of aspiration, the inlet end of the probe. A pulse is generated by the appropriate one of detectors 92a-92e which is carried to controller 10 along line 91. In response thereto, a stored program in controller 10 generates a signal along lead 93 to actuate the appropriate one of stop values 94a-94c and buffer valve 96, which stops aspiration of fluid through the probe by traversing conduit 70 through an air segment. Since the valve cuts through air only, no fluid is handled by this action and carryover, i.e., contamination between succeeding liquid segments, is prevented. As selected large air segments pass through conduit 70 at buffer valve 96, the valve is actuated to bisect the air segment by introducing a segment of buffer B through buffer injection port 98.

FIG. 3A illustrates a preferred embodiment of a fluid "test package" established by the metering apparatus of FIG. 3 and including, in order, a sample S segment which combines as shown with first reagent $R_1$ segment, small air segment $A_1$, a second reagent $R_2$ segment and a large air segment $A_2$, which is divided into equal segments $A_{2'}$ and $A_{2''}$ by a segment of buffer B. The introduction of buffer B further insures against unwanted carryover. Sample S is first aspirated and, immediately thereafter, reagent $R_1$ is aspirated with no intervening air segment. These two liquids are thus permitted to commingle and form a substantially homogeneous single segment. The two reagents, reagents $R_1$ and $R_2$, are introduced in substantially equal amounts, usually about 7.0 microliters (ul). The volume of aspirated sample S is much less than that of either reagent, usually about 1.0 ul. The volume ratio of the small and large air segments is preferably about 1:10, rather than the proportions used for illustration, and usually about 0.5 ul:5.0 ul. The aliquot of buffer B is usually about 2.0 ul.

Successive test packages are thus created and flowed along a single channel of a continuous flow analytical system. The metering apparatus and method of providing the sucessive "test packages" are more fully described in a co-filed application entitled, "CONTINUOUS FLOW METERING APPARATUS", now U.S. Pat. No. 4,517,302 and assigned to the instant assignee.

FIGS. 4A-4E depict the passage of the related segments of a single test package from the narrow section 102 of a segment combining zone 100, through a flotation zone 104, and into an enlarged mixing section 106. The ratio of the inner diameters of narrow section 102 and enlarging mixing section 106 can be from about 1:1.5 to about 1:3. The inner surface of conduit 70, including segment combining zone 100, is coated throughout with an immiscible liquid IL, which preferentially wets the inner surface, preventing contact of a segment therewith.

Figure 4A:
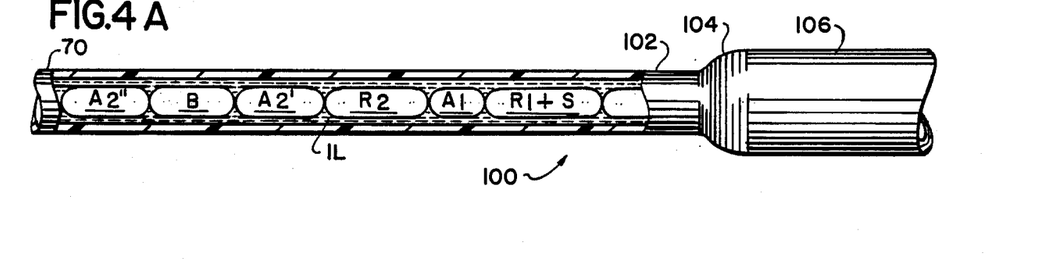
FIGS. 4–4E are sequential diagrammatic views illustrating the combination of separated liquid segments and immiscible segments along the conduit as contemplated by a preferred embodiment of the invention.
Figure 4B:
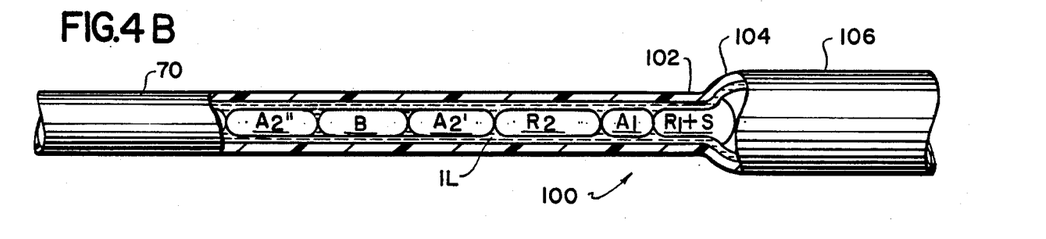

The segments so created are shown, in order, at a cut-away portion of conduit 70. Sample S and first reagent $R_1$ have been combined, as described, to form a single segment $R_1+S$. Small air segment $A_1$ follows segment $R_1+S$ and keeps it separated from the second reagent segment $R_2$. Second reagent segment $R_2$ is followed by the first portion $A_{2'}$ of the large air segment buffer, segment B and then the second portion $A_{2''}$ of the large air segment. Air segment portions $A_{2'}$, B and $A_{2''}$ keep the preceding reactive segments of each test package separated from subsequent test packages. The fluid stream is flowing in the direction indicated by the arrow, as depicted in FIG. 4A. As shown in FIG. 4B, the $R_1+S$ segment flows into flotation zone 104 and is followed by small air bubble $A_1$.

Figure 4C:
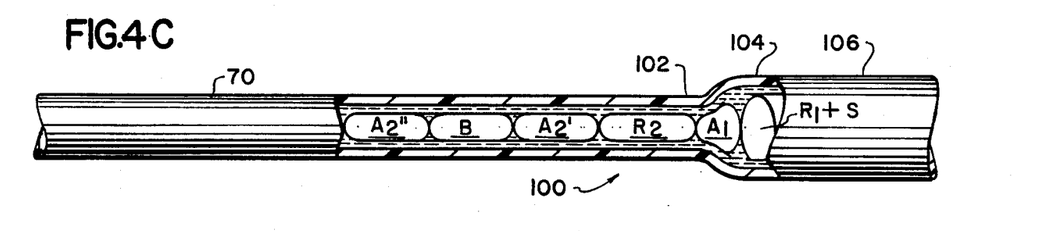

FIG. 4C illustrates the movement of small air bubble $A_1$ into flotation zone 104. Small air bubble $A_1$ is losing contact with the lower surface of the inner wall and beginning to rise in the flotation zone 104. It is just after this point that occlusion is negated.

Figure 4D:
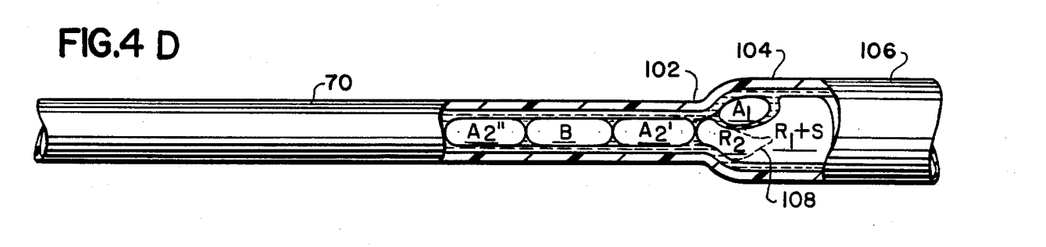

As shown in FIG. 4D, small air segment $A_1$ has ceased to occlude and floated to the top of flotation zone 104. Segment $R_2$ passes into flotation zone 104 and begins to mix with segment $R_1+S$, as shown by phantom line 108. A new segment, which is the combination of segments $R_1+S$ and $R_2$, is thus formed. Following combination of the segments, mixing of and the reaction therebetween begins. Air segment $A_2'$ is about to enter flotation zone 104.

Figure 4E:
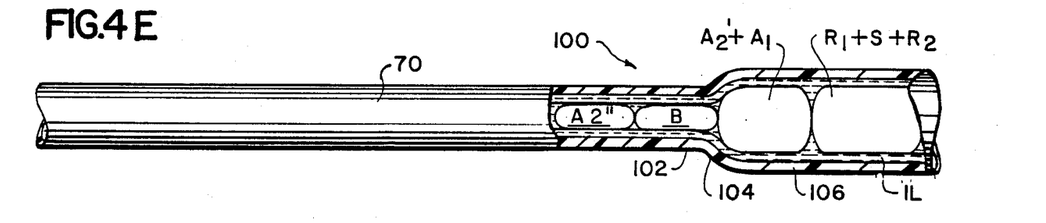

In FIG. 4E, small air segment $A_1$ has coalesced with air segment $A_2'$ to form air segment $A_2'+A_1$. The "combined" air and liquid segments followed by the segment of buffer B and air segment $A_2''$ travel through enlarged section 106, the combined liquid segment being continuously mixed as it travels. It is thereafter analyzed by a colorimeter or ion selective electrode.

The structure and procedure used in this embodiment can be applied to a series of such flotation zones along a conduit. For example, the mixed liquid segment formed by combining two segments, each having a different reaction mixture components, can be made to combine with another liquid segment which follows a "combined" air segment. To achieve this, another enlargement can provide a floation zone in which the combined air segment is non-occluding. A liquid segment following the combined air segment is thereby caused to combine with the mixed liquid segment which was established at the first flotation zone.

In another embodiment, not illustrated, separated liquid segments, e.g., corresponding to $R_1+S$ and $R_2$, are brought together by fragmenting the intervening air segment into a plurality of smaller bubbles. These small bubbles float freely in the segment which is the combination of the previously separated segments and do not occlude the conduit or interfere with mixing of components from the previously separated segments. Various techniques can be used to fragment the occluding air segment. These include, for example, physically striking the tubing, vibrating the tubing with external mechanical apparatus or vibrating the segment by passing disruptive energy waves, such as sound waves, therethrough.

Figure 5A:
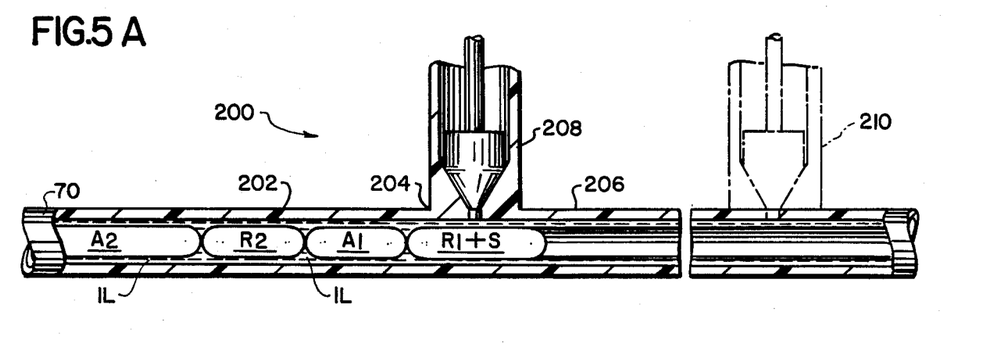
Figure 5B:
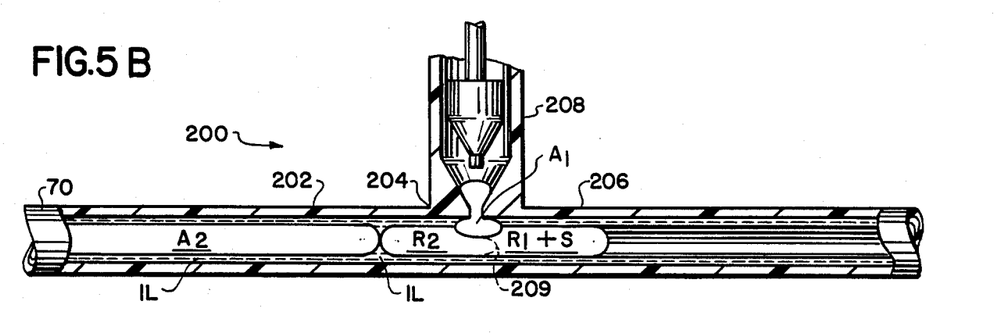
Figure 5C:
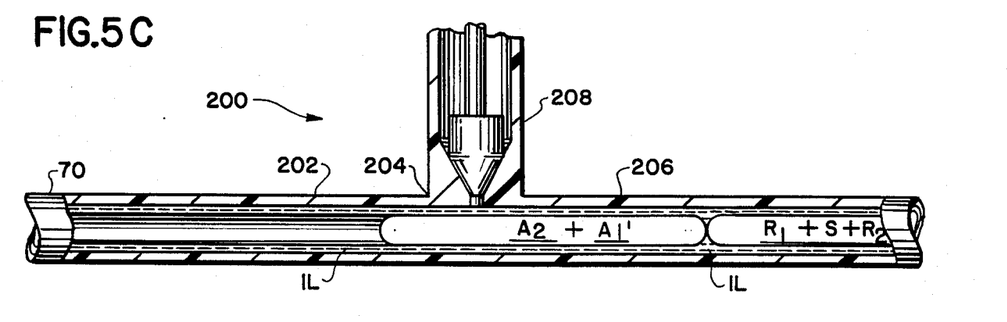

Yet another embodiment of the invention is contemplated which differs from the above embodiments by providing for the physical removal of at least a portion of the intervening air segment so as to render the same non-occluding. This may be accomplished by a semipermeable or porous section of conduit wall, any of a number of various valve arrangements, or other means, such as a debubbler, which connect with the flow path of the conduit. One example of this embodiment is illustrated by FIGS. 5A–5C. FIG. 5A depicts the pasage of a single test package from a first section 202 of a segment removal zone 200, through a second section 204, which contains a poppet valve 208, and into a third section 206. The inner surface of conduit 70 is coated throughout with immiscible liquid IL. The tip of the poppet valve conforms to or defines a portion of the inner wall surface of conduit 70 when in a closed position, to facilitate the reformation of the immiscible liquid IL layer. A liquid segment $R_1+S$, containing a first reagent $R_1$ and a sample S to be analyzed, is followed by a small air bubble $A_1$. Next is a liquid segment containing second reagent $R_2$ which is reactive with liquid segment $R_1+S$ to provide a detectable response. The last segment is a large air segment $A_2$ which separates the above segments from the next successive test package.

FIG. 5B illustrates the passage of a portion of small air segment $A_1$ into second section 204. At this point, poppet valve 208 is operated, aspirating at least a portion of small air segment $A_1$, thereby rendering it non-occluding along the remainder of the conduit. The remaining portion of small air bubble $A_1$ has lost contact with the lower surface of the inner wall. Segment $R_2$ enters second section 204 and begins to mix with segment $R_1+S$, as shown by phantom line 209. A new segment is thus formed which is the combination of segments $R_1+S$ and $R_2$. Following combination of the liquid segments, mixing of and the reaction between $R_1$, $R_2$ and S begins. Large air bubble $A_2$ is about to enter second section 204.

In FIG. 5C, air bubble fragment $A_1'$ is all that remains of small air segment $A_1$. Air fragment $A_1'$ momentarily remains stationary, is contacted by and combines with large air segment $A_2$ to form combined air segment $A_2+A_1'$ which travels through the third section 206. The combined liquid segment is continuously mixed as it travels through third section 206. It is thereafter analyzed by any of numerous conventional methods, some of which are identified below.

The structure and procedure used in this embodiment can be applied using a series of such aspiration apparatus along the same conduit. Referring again to FIG. 5A, a second poppet valve 210 (shown in phantom) is positioned downstream of poppet valve 208. Combined segment $R_1+S+R_2$ formed in the first test package can be made to later combine with another liquid segment or sequence of segments, which follows combined air segment $A_1+A_2$. Aspiration of a sufficient portion of combined air segment $A_1+A_2$ by operation of poppet valve 210 renders it non-occlusive. A liquid following air segment $A_2$ is thereby caused to mix with combined segment $R_1+S+R_2$, which was combined by operation of poppet valve 208.

Figure 6:
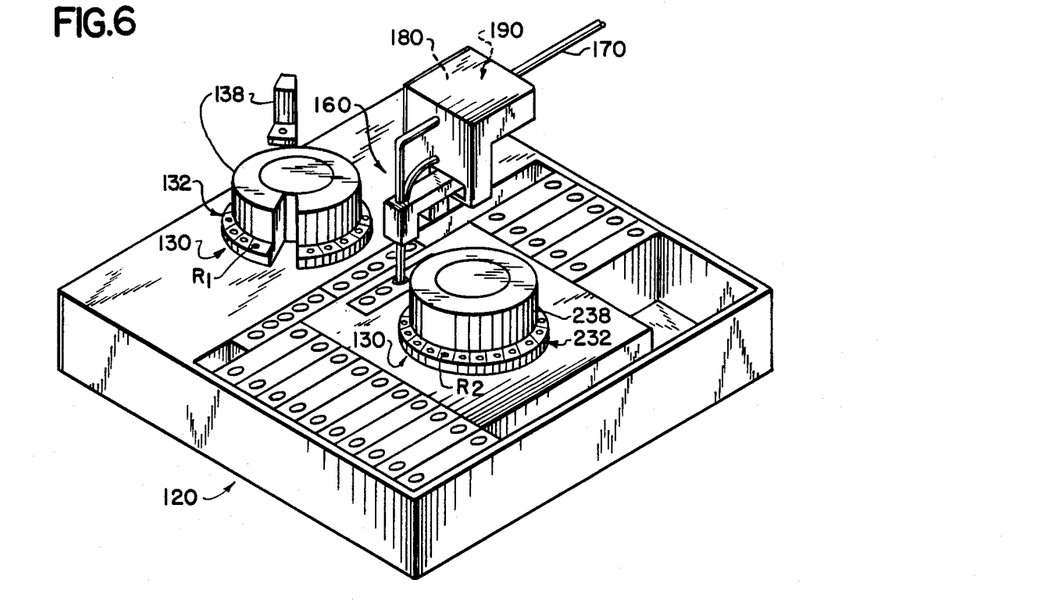
FIG. 6 illustrates another embodiment of the single channel continuous flow system of the invention in which related first and second reagents are respectively disposed in separate reagent dispensers on separate reagent turntables.

FIG. 6 illustrates an alternate embodiment of the front end of the system in which all of the first reagents $R_1$ for the assays to be performed are in single well reagent dispensers 138 positioned on a first reagent turntable 132 which is connected to bidirectional rotation drive means (not shown). All of the second reagents $R_2$ for the assays to be performed are in single well reagent dispensers 238 positioned on a second reagent turntable 232 which is connected to another bidirectional rotation drive means (not shown). The drive means are independently activated by a controller (not shown), such as the one previously described, to impart a metered rotation of reagent turntable 132 or 232 as needed to present a selected reagent dispenser 138 or 238, respectively, for aspiration of liquid therefrom and into conduit 170. As in previously described embodiments, a controller coordinates the operation of sample assembly 120, reagent assembly 130, probe assembly 160, immiscible liquid IL dispenser assembly 180 and metering assembly 190. Each of these components is substantially as described with reference to earlier drawings, as is the sequence of aspiration and system operation.

Figure 7:
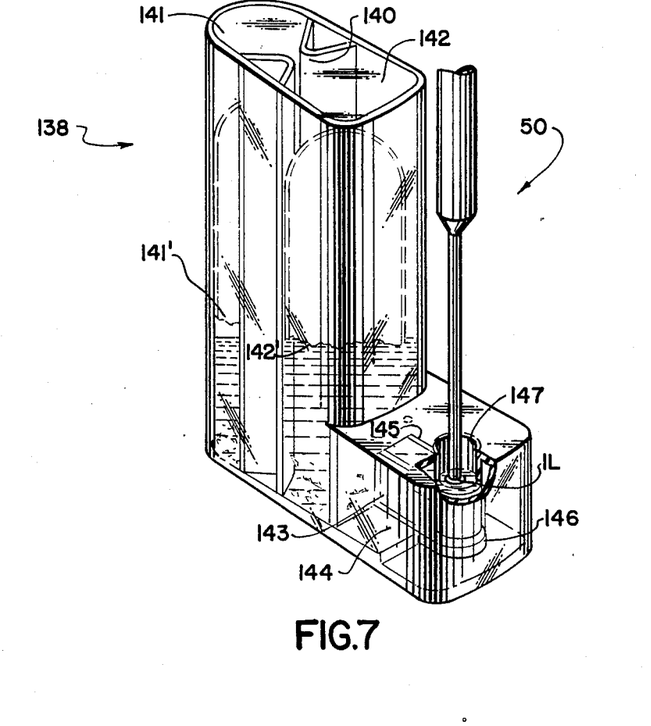
FIG. 7 is an enlarged view of the reagent dispenser illustrated in FIG. 6.

FIG. 7 illustrates reagent dispenser 138 in greater detail. The structure of reagent dispenser 238 are substantially identical, but for the reagent and reconstituting liquid packaged therein. Thus, reagent dispenser 138 will be described as exemplary of both. Reagent dispenser 138 includes a reagent reservoir 140 which encloses two breakable capsules 141 and 142, respectively containing lyophilized reagent 141' and reconstituting liquid 142', usually a buffer. Reservoir 140 has flexible side walls which permit external pressure to break capsules 141 and 142. When reagent dispenser 138 is positioned on a turntable, the reagent in reservoir 140 flows through port 143 into reagent trough 144, defined by side walls 145. At the other end of trough 144 is filter 146. A fluid level equilibrium is established between reservoir 140 and dispensing well 147.

A drop of immiscible liquid IL is positioned on the meniscus, either manually or from an immiscible liquid dispenser. Reagent dispenser 138 operates in the same manner as that described for either of the first reagent $R_1$ or section reagent $R_2$ dispensing components of the two reagent dispenser previously described. Reagent dispenser 138 is another preferred embodiment of the reagent package which is the subject of a co-filed application entitled, "INTEGRAL REAGENT DISPENSER", referred to above.

The detector assembly provided in the system of the invention measures a characteristic of or other detectable response associated with the original sample by appropriate analytical techniques. Examples are electromagnetic radiation such as fluorescence, phosphorescence, chemiluminescence, changes in light absorption, reflectance or scattering in the visible, ultraviolet or infrared ranges. Also included is any observable change in a system parameter such as a change in or appearance of a reactant, observable precipitation or agglutination of any component in the reaction mixture as well as one which is detectable through the senses directly or by the use of ancillary detection means.

After the analytical result, such as a reaction product, is obtained as a detectable change, it is measured, usually by passing the reaction mixture through a zone in which suitable apparatus for reflection, emission transmission, scattering or fluorescence photometry is provided. Such apparatus serves to direct a beam of energy, such as light, through the conduit. The light then passes to a detector. Generally, electromagnetic radiation in the range of from about 200 to about 900 nanometers (nm) has been found useful for such measurements, although any radiation to which the conduit and reaction mixture are permeable and which is capable of quantifying the response provided can be used. Such detection means can include instruments such as spectrophotometers, ultraviolet light-sensing equipment, fluorometers, spectrofluorometers, nephelometers, turbidimeters, pH meters or electrodes.

Although the invention has been described with particularity, numerous changes in the details, combinations and arrangements of elements may be resorted to without departing from the scope of the invention.

What is claimed is:

1. A method of reacting discrete liquid segments passing through sequential first, second and third sections of a single conduit, which method comprises the steps of:
   (a) introducing and passing a first segment of a liquid sample and a second segment of a liquid reagent separated by a first gas segment into and along said first conduit section;
   (b) forming the first gas segment to occlude said first conduit section to maintain the first and second liquid segments separate while in said first conduit section;
   (c) rendering the first gas segment ineffective to occlude said second conduit section to combine in said second conduit section the first and second liquid segments, which had been previously maintained separate in said first conduit section, to provide a combined liquid segment;
   (d) completely mixing the combined liquid segment in said third conduit section;
   (e) receiving the completely mixed combined liquid segment and the gas segment from said third conduit section; and
   (f) analyzing the completely combined liquid segment.

2. The method of claim 1 wherein said rendering step comprises removing the first gas segment through valving means in said second conduit section.

3. The method of claim 1 wherein said rendering step comprises forming said second conduit section of a diameter sufficient to render the first gas segment non-occlusive therein.

4. The method of claim 1 wherein said rendering step comprises removing a portion of the first gas segment from said second conduit section without removing liquid from the first and second liquid segments.

5. The method of claim 1 wherein said introducing step comprises introducing the first and second liquid segments and the first gas segment into a single probe connected to the inlet of said first conduit section.

6. The method of claim 5 wherein said introducing step comprises:
   (a) introducing the first liquid segment mixed with a first reagent therefor;
   (b) then introducing the first gas segment;
   (c) then introducing the second liquid segment;
   which comprises the additional steps of forming the second gas segment to occlude said first and second conduit sections and which combines with said first gas segment to occlude said third conduit segment and analyzing the completely mixed combined liquid segment.

7. A method for reacting and analyzing liquid segments in a stream of an alternating sequence of gas and liquid segments flowing along a single conduit, which method comprises:
   (a) maintaining a continuous film of liquid fluorocarbon on the inner surface of a conduit having a single inlet and sequential first, second and third sections;
   (b) introducing into said inlet a first liquid segment of about 1 ul of a blood serum sample to be analyzed and mixed with about 7 ul of a first reagent which is reactive therewith;
   (c) following (b), introducing into said inlet a first air segment which is occlusive in said inlet and said first conduit section;
   (d) following (c), introducing into said inlet a second liquid segment of about 7 ul of a second reagent which is reactive with a reaction product of the sample and the first reagent to give a detectable response;
   (e) following (d), introducing into said inlet a second air segment which is occlusive in said inlet and said first, second and third conduit sections;
   (f) maintaining the first and section liquid segments separated by the first gas segment while in said inlet and first conduit section;

(g) passing said first and second liquid segments which had been maintained separate in said first conduit section into said second conduit, said second conduit section being formed to have a diameter sufficient to render the first gas segment non-occlusive in said second conduit section;

(h) combining the first and second liquid segments in said second conduit section to provide a combined liquid segment;

(i) coalescing the first and second gas segments in said second conduit section to form a coalesced gas segment which is occlusive in said second and third conduit sections;

(j) completely mixing the combined liquid segment in said third conduit section; and (k) analyzing the completely mixed combined liquid segment while passing through said third conduit section.

8. A single channel analytical system for analysis of selected liquid segments in a continuously flowing stream of an alternating sequence of gas and liquid segments, which system comprises:

(a) a single solid fluorocarbon conduit having an inner surface and having first, second and third sequential sections and a single inlet;

(b) a single probe in fluid communication with said conduit inlet;

(c) means cooperating with said conduit and said probe for maintaining on said inner surfaces of said conduit and said probe a continuous film of a liquid fluorocarbon;

(d) a pump cooperating with said conduit for introducing a fluid stream into said probe and passing said stream along said conduit through said inlet;

(e) a metering apparatus for introducing into said probe and first conduit section a plurality of test packages, each of which comprises a first liquid segment of about 1 ul of a blood serum sample to be analyzed mixed with 7 ul of a first reagent which is reactive therewith, a first air segment, which is occlusive in said first conduit section, a second liquid segment of about 7 ul of a second reagent which is reactive with a reaction product of said sample and said first reagent to give a detectable response, and a second air segment;

(f) means for combining the first and second liquid segments and for coalescing the first and second air segments comprising said second conduit section having a diameter sufficiently greater than that of said first conduit section to render the first gas segment non-occlusive, thereby combining the first and second liquid segments, which had been separately introduced into said inlet and previously maintained separate along said first conduit section to provide a combined liquid segment;

(g) said third conduit section comprising means for completely mixing the combined liquid segments; and (h) means for analyzing the combined liquid segments along said third conduit section and comprising at least one colorimeter.

9. A system for continuous flow of an alternating sequence of gas and liquid segments, which system comprises:

(a) a conduit having an inner surface and having first, second and third sequential sections and a single inlet;

(b) means cooperating with said conduit for maintaining on said inner surface of said conduit a continuous film of an immiscible liquid which preferentially wets said inner surface to the exclusion of the gas and liquid segments;

(c) means for passing a fluid package comprising in sequence a first liquid segment, a first gas segment, a second liquid segment and a second gas segment through said inlet and along said first conduit section, one of the first and second liquid segments being a reagent or diluent liquid for the other of the first and second liquid segments which defines a liquid sample to be analyzed;

(d) means for combining the first and second liquid segments of the fluid package, which had been separately passed into said first conduit section and previously maintained separate therein, along said conduit section having completely closed walls, thereby permitting mixing of the first and second liquid segments while passing along said third conduit section to provide a combined liquid segment;

(e) said third conduit section comprising means for completely mixing the combined liquid segment therein; and (f) means for receiving and analyzing the completely mixed liquid segment from said third conduit section.

10. The continuous flow system of claim 9 wherein the ratio range of the inner diameter of said first conduit section to said third conduit section is from about 1:1.5 to about 1:3, said first conduit section sized such that the first gas segment is occlusive therein, said second conduit section sized such that the first gas treatment is non-occlusive in at least a portion thereof and said third conduit section sized such that the first gas segment is non-occlusive therein.

11. The continuous flow system of claim 10 wherein said second conduit section is of a diameter greater than that of said first conduit section and sufficient to render the first gas segment non-occlusive.

* * * * *